United States Patent
Kuzma

[19]

[11] Patent Number: 6,038,484
[45] Date of Patent: Mar. 14, 2000

[54] COCHLEAR ELECTRODE WITH MODIOLAR-HUGGING SYSTEM INCLUDING A FLEXIBLE POSITIONER

[75] Inventor: Janusz A. Kuzma, Englewood, Colo.

[73] Assignee: Advanced Bionics Corporation, Sylmar, Calif.

[21] Appl. No.: 09/140,034

[22] Filed: Aug. 26, 1998

Related U.S. Application Data

[60] Provisional application No. 60/087,655, Jun. 2, 1998, provisional application No. 60/079,676, Mar. 27, 1998, provisional application No. 60/067,534, Dec. 4, 1997, provisional application No. 60/061,945, Oct. 14, 1997, and provisional application No. 60/056,055, Sep. 2, 1997.

[51] Int. Cl.[7] ........................................................ A61N 1/05
[52] U.S. Cl. ............................................................. 607/137
[58] Field of Search ..................................... 607/136, 137, 607/55–57; 600/585, 379; 606/129

[56] References Cited

U.S. PATENT DOCUMENTS

| | | |
|---|---|---|
| 4,284,085 | 8/1981 | Hansen et al. ............................ 607/137 |
| 4,819,647 | 4/1989 | Byers et al. . |
| 4,832,051 | 5/1989 | Jarvik et al. . |
| 4,898,183 | 2/1990 | Kuzma . |
| 5,000,194 | 3/1991 | van den Honert et al. . |
| 5,037,497 | 8/1991 | Stypulkowski . |
| 5,443,493 | 8/1995 | Byers et al. . |
| 5,545,219 | 8/1996 | Kuzma . |
| 5,578,084 | 11/1996 | Kuzma et al. . |
| 5,603,726 | 2/1997 | Schulman et al. . |
| 5,645,585 | 7/1997 | Kuzma . |
| 5,649,970 | 7/1997 | Loeb et al. . |
| 5,653,742 | 8/1997 | Parker et al. . |
| 5,667,514 | 9/1997 | Heller . |

FOREIGN PATENT DOCUMENTS 9631087  3/1996  WIPO .

*Primary Examiner*—William E. Kamm
*Assistant Examiner*—George R. Evanisko
*Attorney, Agent, or Firm*—Bryant R. Gold

[57] ABSTRACT

An electrode system includes (1) an electrode array, made in a straight or curved shape, but made on a flexible carrier so that it can easily bend within a curved body cavity, such as the cochlea; and (2) a flexible positioner, typically molded in a curved shape from a silicone polymer so as to make it easy to slide into the body cavity. Some embodiments may further include an electrode guiding insert. Yet other embodiments include only a flexible positioner adapted to fill space within a human cochlea so as to force an electrode array against a modiolar wall of the cochlea. Insertion of the electrode array is performed using one of two methods. A first method involves first inserting the flexible positioner into the scala tympani (one of the channels of the cochlea) to a desired depth, which desired depth typically involves a rotation of about 360 degrees and causes the positioner to rest against the outer or lateral wall of the scala tympani, leaving an opening slightly larger than the cross-section of the electrode array adjacent the inner wall of the scala tympani, and then second inserting the electrode array into the opening defined by the positioner and inner wall. The guiding insert may be used, in some embodiments, to assist guiding the electrode array into this opening. A second method of insertion involves first inserting an electrode array into the scala tympani, and then second inserting the positioner into the scala tympani so as to lie between the electrode array and the outer wall of the scala tympani, thereby forcing the electrode array against the inner wall of the scala tympani. Insertion of the positioner into scala tympani after the electrode array has been at least partially inserted therein further carries the electrode array deeper into the scala tympani to a desired final position, and maintains it in that position.

18 Claims, 11 Drawing Sheets

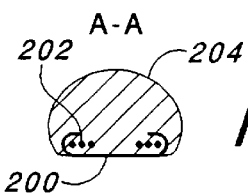
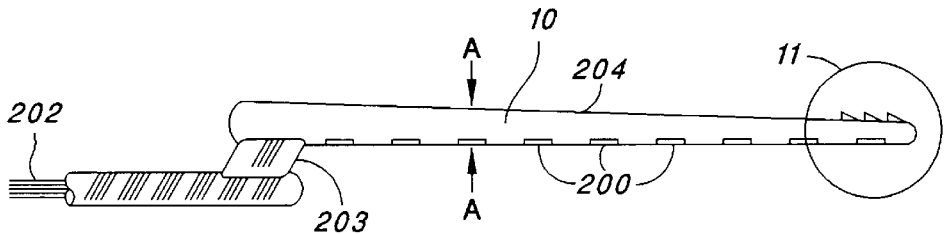
FIG. 1B
FIG. 1A
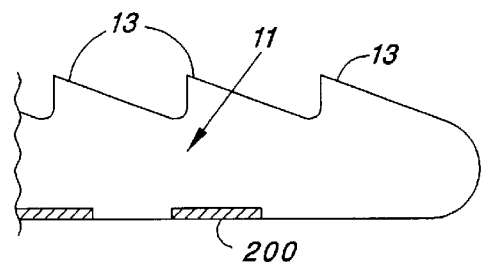
FIG. 1C
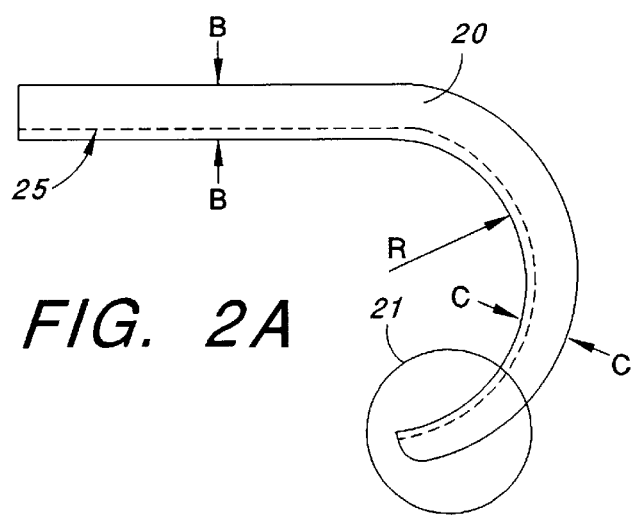
FIG. 2A
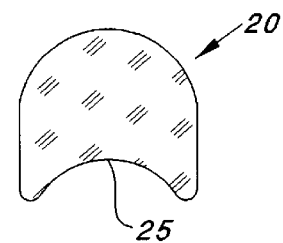
FIG. 2C
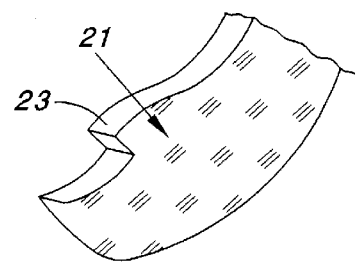
FIG. 2B

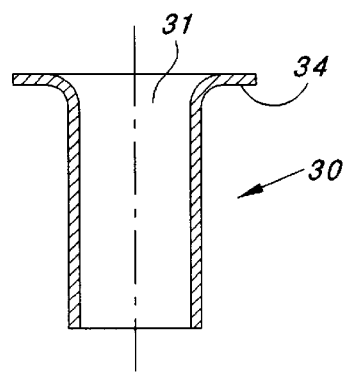
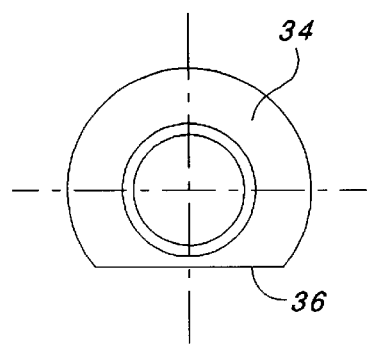
FIG. 3A            FIG. 3B
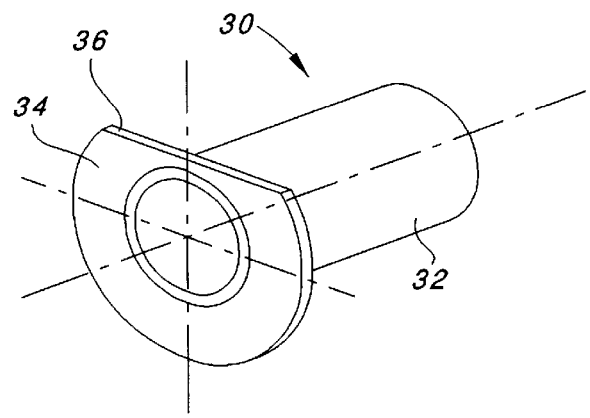
FIG. 3C
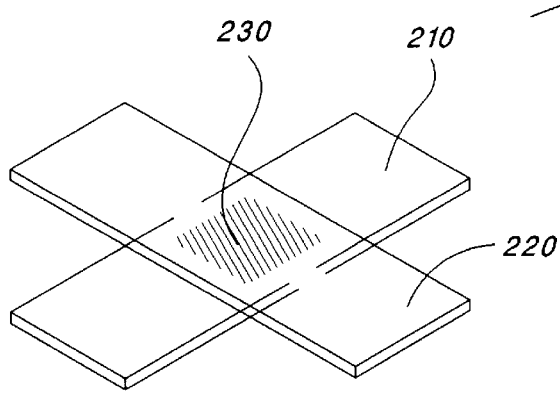
FIG. 7B
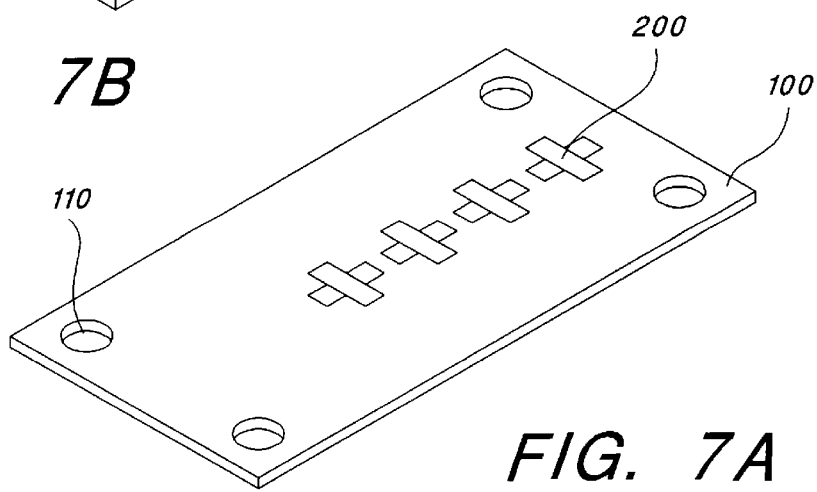
FIG. 7A

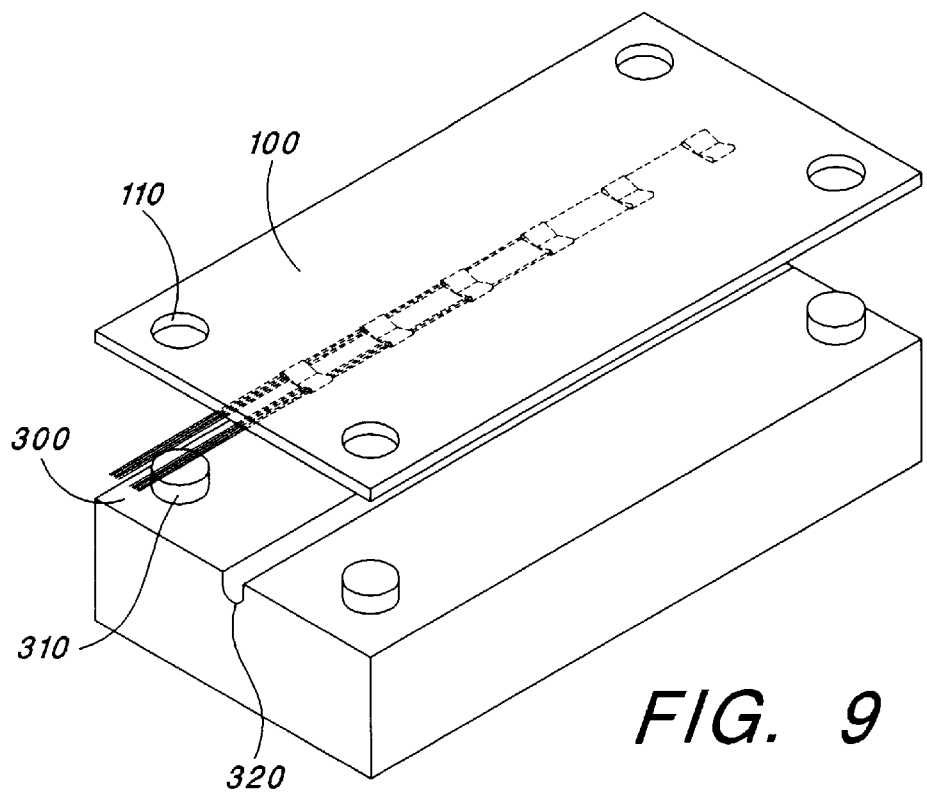
FIG. 9
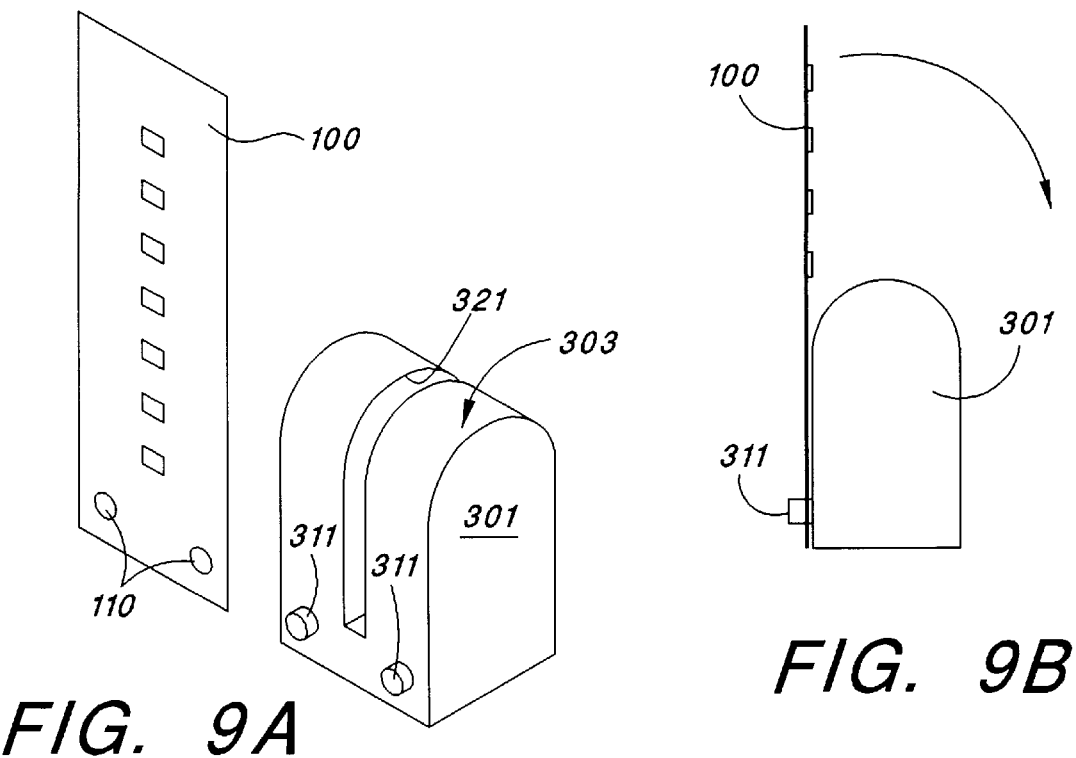
FIG. 9A
FIG. 9B

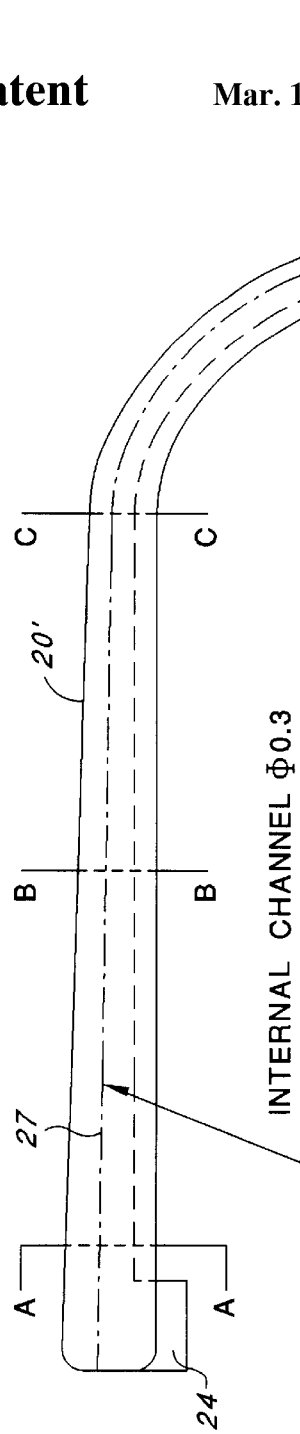
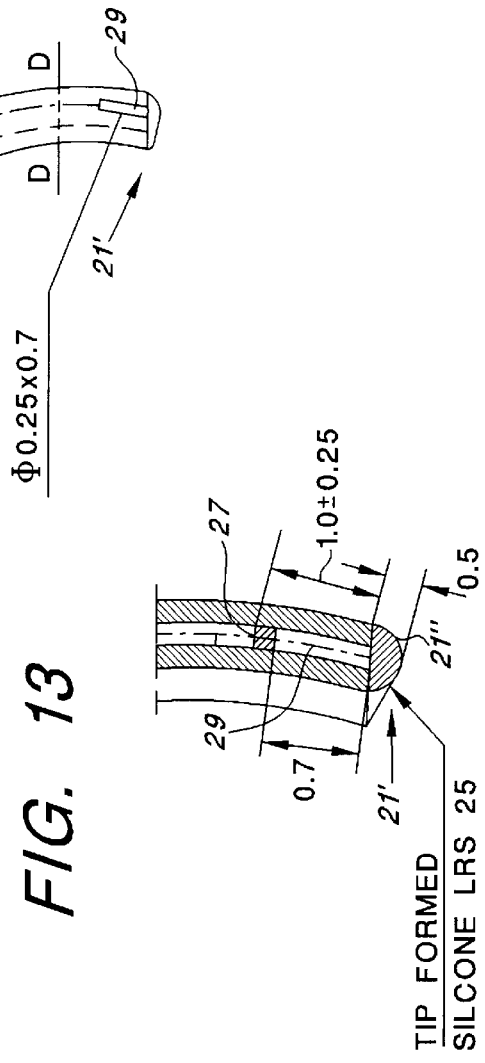
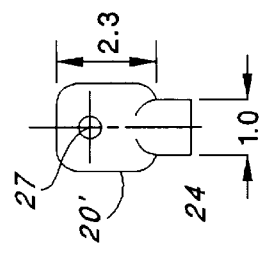
FIG. 13
FIG. 14A
FIG. 14B

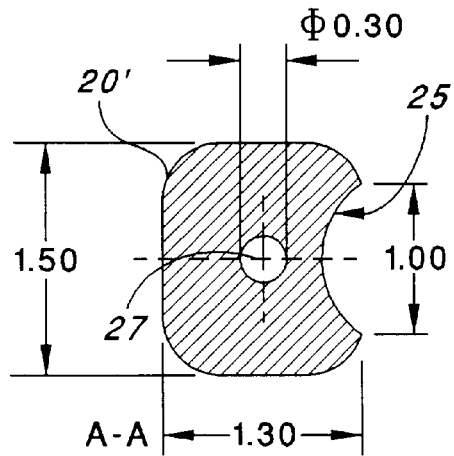
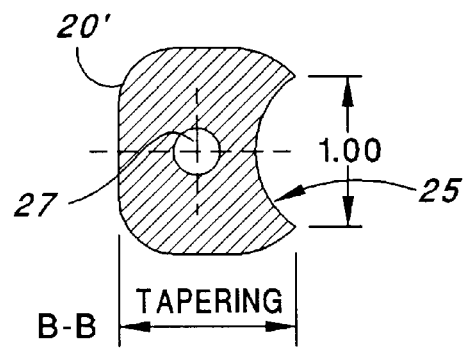
FIG. 13A    FIG. 13B
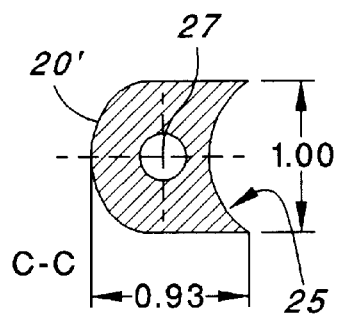
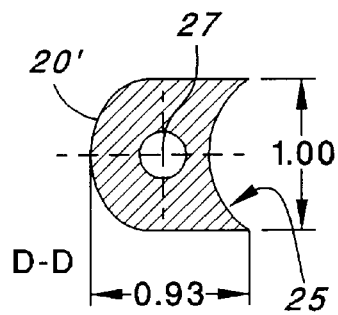
FIG. 13C    FIG. 13D
MATERIAL: LSR 70, LSR 25, Pt 99.5%

COCHLEAR ELECTRODE WITH MODIOLAR-HUGGING SYSTEM INCLUDING A FLEXIBLE POSITIONER

This application claims the benefit of the following U.S. Provisional patent applications: Ser. No. 60/087,655, filed Jun. 2, 1998; Ser. No. 60/079,676, filed Mar. 27, 1998; Ser. No. 60/067,534, filed Dec. 4, 1997; Ser. No. 60/061,945, filed Oct. 14, 1997; and Ser. No. 60/056,055, filed Sep. 2, 1997; all of which patent applications are incorporated herein by reference.

BACKGROUND OF THE INVENTION

The present invention relates to implantable stimulation devices, e.g., cochlear prosthesis used to electrically stimulate the auditory nerve, and more particularly to an electrode array for use with a cochlear stimulator that is designed to hug the modiolus so as to place electrode contacts of the electrode array in close proximity to the ganglion cells and thereby to the auditory nerve fibers.

Hearing loss, which may be due to many different causes, is generally of two types: conductive and sensorineural. Of these, conductive hearing loss occurs where the normal mechanical pathways for sound to reach the hair cells in the cochlea are impeded, for example, by damage to the ossicles. Conductive hearing loss may often be helped by use of conventional hearing aids, which amplify sound so that acoustic information does reach the cochlea and the hair cells. Some types of conductive hearing loss are also amenable to alleviation by surgical procedures.

In many people who are profoundly deaf, however, the reason for their deafness is sensorineural hearing loss. This type of hearing loss is due to the absence or the destruction of the hair cells in the cochlea which are needed to transduce acoustic signals into auditory nerve impulses. These people are unable to derive any benefit from conventional hearing aid systems, no matter how loud the acoustic stimulus is made, because their mechanisms for transducing sound energy into auditory nerve impulses have been damaged. Thus, in the absence of properly functioning hair cells, there is no way auditory nerve impulses can be generated directly from sounds.

To overcome sensorineural deafness, there have been developed numerous cochlear implant systems—or cochlear prosthesis—which seek to bypass the hair cells in the cochlear (the hair cells are located in the vicinity of the radially outer wall of the cochlea) by presenting electrical stimulation to the auditory nerve fibers directly, leading to the perception of sound in the brain and an at least partial restoration of hearing function. The common denominator in most of these cochlear prosthesis systems has been the implantation into the cochlea of electrodes which are responsive to a suitable external source of electrical stimuli and which are intended to transmit those stimuli to the ganglion cells and thereby to the auditory nerve fibers.

A cochlear prosthesis operates by direct electrical stimulation of the auditory nerve cells, bypassing the defective cochlear hair cells that normally transduce acoustic energy into electrical activity in such nerve cells. In addition to stimulating the nerve cells, the electronic circuitry and the electrode array of the cochlear prosthesis performs the function of separating the acoustic signal into a number of parallel channels of information, each representing the intensity of a narrow band of frequencies within the acoustic spectrum. Ideally, each channel of information would be conveyed selectively to the subset of auditory nerve cells that normally transmitted information about that frequency band to the brain. Those nerve cells are arranged in an orderly tonotopic sequence, from high frequencies at the basal end of the cochlear spiral to progressively lower frequencies towards the apex. In practice, this goal tends to be difficult to realize because of the anatomy of the cochlea.

Over the past several years, a consensus has generally emerged that the scala tympani, one of the three parallel ducts that, in parallel, make up the spiral-shaped cochlea, provides the best location for implantation of an electrode array used with a cochlear prosthesis. The electrode array to be implanted in this site typically consists of a thin, elongated, flexible carrier containing several longitudinally disposed and separately connected stimulating electrode contacts, perhaps 6–30 in number. Such electrode array is pushed into the scala tympani duct to a depth of about 20–30 mm via a surgical opening made in the round window at the basal end of the duct. During use, electrical current is passed into the fluids and tissues immediately surrounding the individual electrical contacts in order to create transient potential gradients that, if sufficiently strong, cause the nearby auditory nerve fibers to generate action potentials. The auditory nerve fibers arise from cell bodies located in the spiral ganglion, which lies in the bone, or modiolus, adjacent to the scala tympani on the inside wall of its spiral course. Because the density of electrical current flowing through volume conductors such as tissues and fluids tends to be highest near the electrode contact that is the source of such current, stimulation at one contact site tends to activate selectively those spiral ganglion cells and their auditory nerve fibers that are closest to that contact site. Thus, there is a need for the electrode contacts to be positioned as close to the ganglion cells as possible. This means, in practice, that the electrode array, after implant, should preferably hug the modiolar wall, and that the individual electrodes of the electrode array should be positioned on or near that surface of the electrode array which is closest to the modiolar wall.

In order to address the above need, it is known in the art to make an intracochlear electrode array that includes a spiral-shaped resilient carrier which generally has a natural spiral shape so that it better conforms to the shape of the scala tympani. See, e.g., U.S. Pat. No. 4,819,647. The '647 U.S. patent is incorporated herein by reference. Unfortunately, while the electrode shown in the '647 patent represents a significant advance in the art, there exists lack of sufficient shape memory associated with the electrode to allow it to return to its original curvature (once having been straightened for initial insertion) with sufficient hugging force to allow it to wrap snugly against the modiolus of the cochlea.

It is also known in the art, as shown in applicant's prior patents, U.S. Pat. Nos. 5,545,219 and 5,645,585, to construct an electrode carrier from two initially straight members, a rodlike electrode carrier and a flexible rodlike positioning member. As shown in these patents, the two members extend in substantially parallel relation to and closely alongside each other, but are connected to each other only at their respective leading and trailing end regions. After implant, a pushing force is applied to the positioning member so that it is forced to assume an outwardly arched configuration relative to the electrode carrier, thereby forcing the electrode carrier into a close hugging engagement with the modiolus, thereby placing the electrode contacts of the electrodes in as close a juxtaposition to the cells of the spiral ganglion as possible. The '219 and '585 U.S. patents are also incorporated herein by reference.

Unfortunately, while the electrode array taught in the above-referenced '219 and '585 patents has the right idea, i.e., to force the electrode carrier into a close hugging engagement with the modiolus, it does so only by use of an additional element that makes manufacture of the lead more difficult and expensive, and only through application of an additional pushing force which is applied to an electrode structure after it is already fully inserted into the cochlea. Such additional pushing force may easily cause damage to the delicate scala tympani. Moreover, the entire electrode array may twist during the insertion process, or when the additional pushing force is applied, thereby causing the electrode contacts to twist and/or be forced away from the modiolus, rather than in a hugging relationship therewith.

Thus, while it has long been known that an enhanced performance of a cochlear implant can be achieved by proper placement of the electrode contacts close to the modiolar wall of the cochlea, two main problems have faced designers in attempting to achieve this goal. First, it is extremely difficult to assemble electrode contacts on the medial side of the an electrode array, facing the modiolus of the cochlea. Second, heretofore there has either been the need for application of an external (and perhaps unsafe) force, or a lack of sufficient shape memory, to allow the electrode (after initial straightening to facilitate insertion) to assume or return to the desired curvature needed to place the electrodes against the modiolar wall so that the curvature wraps snugly around the modiolus of the cochlea. As a result, the electrode contacts of the prior art electrodes are generally positioned too far way from the modiolar wall.

It is thus evident that improvements are still needed in cochlear electrodes, particularly to facilitate assembling an electrode so that the electrode contacts are on the medial side of the electrode array, and to better assure that the electrode assumes a close hugging relationship with the modiolus once implantation of the electrode has occurred.

SUMMARY OF THE INVENTION

The present invention addresses the above and other needs by providing an electrode system that allows for correct positioning of the electrode contacts against the modiolar wall of the cochlea. Such "correct" positioning is achieved through the use of an electrode system that includes at least one of the following three main components: (1) an electrode array, preferably made in a slightly curved shape, for improved stability of electrode contact direction, made on a flexible carrier so that it can easily bend within the cochlea; (2) a flexible positioner, typically molded from a silicone polymer so as to make it easy to slide into the cochlea, and made to assume a curved shape to facilitate its insertion into the cochlea; and (3) an electrode guiding insert made from a biocompatible material, such as platinum (Pt), titanium (Ti) or Teflon.

Insertion of the electrode array is performed in three main steps. First, the flexible positioner is inserted through the appropriate dimension of cochleostomy. This means it is inserted into the scala tympani (one of the channels of the cochlea) to the desired depth. The desired depth typically involves a rotation of about 360 degrees and causes the positioner to rest against the outer or lateral wall of the scala tympani, leaving an opening slightly larger than the cross-section of the electrode array adjacent the inner wall of the scala tympani. Advantageously, the super-flexible nature of the positioner prevents it from causing damage to the cochlear structure. At the same time, once inserted, it provides a guide for the electrode, and protects the cochlear walls from being damaged or touched directly by the stiffer electrode body.

Second, after insertion of the positioner to the desired depth, the guiding insert may be pushed into the opening of the cochlea.

Third, the electrode array is inserted through the opening of the guiding insert to the desired depth. This desired depth is preferably beyond the depth of the positioner. The distal end of the array advantageously includes engaging or locking barbs that engage with corresponding barbs at the distal end of the positioner. At this stage, the electrode is positioned very close to the modiolus of the cochlea. Then, as a final optimization of the position of the electrode contacts of the electrode array, the electrode array is pulled back slightly (about 2 mm). This backward motion assures that the distal tips of the electrode array and the positioner are engaged by the barbs located thereon. Such engagement may further serve to force the electrodes into direct contact with the modiolar wall.

Advantageously, the electrode system of the present invention achieves the following goals: (1) it virtually guarantees that the electrode array will be optimally positioned against the modiolar wall in a cochlea of any size; (2) the insertion of the electrode array avoids or produces minimal trauma to the cochlear structure; (3) it allows deep insertion beyond 360 degrees; (4) it can be manufactured using easy, low cost technology; and (5) the electrode can be easily removed and reinserted, if required.

In accordance with an alternate embodiment of the invention, there is provided an electrode positioner that may be used with almost any electrode array that is to be inserted into the cochlea in order to assure that a desired modiolar-hugging position is achieved with the electrode contacts of the array.

In accordance with yet an additional embodiment of the invention, a cochlear electrode system is provided that includes (1) an electrode array and (2) an electrode positioner. Using a preferred insertion technique or method, the electrode array is first inserted into the cochlea as far as it reasonably can be; then the positioner is inserted into the cochlea, behind the electrode array so as to force or push the electrode contacts of the array against the modiolar wall. Moreover, as the positioner is thus inserted into the cochlea behind the electrode array, the positioner carries the electrode deeper into the cochlea, e.g., approximately ½ turn deeper. In such instance, the positioner need not be equipped with internal barbs at its distal end.

BRIEF DESCRIPTION OF THE DRAWINGS

The above and other features and advantages of the present invention will be more apparent from the following more particular description thereof, presented in conjunction with the following drawings wherein:

FIGS. 1A and 1B show a side and cross-sectional view, respectively, of an electrode array which forms part of the electrode system of the present invention;

FIG. 1C illustrates an enlarged view of the engaging barbs used at a distal end of the electrode array shown in FIG. 1A;

FIGS. 2A and 2B show a side and cross-sectional view, respectively, of a curved positioner that forms part of the electrode system of the present invention;

FIG. 2C depicts an enlarged view of a distal end of the positioner shown in FIG. 2A;

FIGS. 3A, 3B and 3C illustrate a cross-sectional, top, and perspective view, respectively, of an insert that forms part of the electrode system of the present invention, which insert is used to guide the electrode as it is inserted into the cochlea;

FIG. 7A depicts a preferred manner of making a multi-electrode electrode array of the type shown in FIG. 1A;

FIG. 7B shows an enlarged view of the electrode contacts of the array of FIG. 1A;

FIG. 9 depicts a molding die onto which the partially-formed electrode array of FIG. 7A, with wires attached to each of the electrodes as shown in FIGS. 8A–8D, may be mounted in order to form a polymer carrier for the electrode array;

FIG. 9A and 9B illustrate an alternative type of molding die onto which the partially-formed electrode array of FIG. 7A, with wires attached to each of the electrodes as shown in FIGS. 8A–8D, may be mounted in order to form a polymer carrier for the electrode array;

FIG. 13 illustrates a side profile view of an alternative embodiment of a positioner made in accordance with the invention;

FIG. 13A is a sectional view taken along the lines A—A of the positioner of FIG. 13;

FIG. 13B is a sectional view taken along the line B—B of the positioner of FIG. 13;

FIG. 13C is a sectional view taken along the line C—C of the positioner of FIG. 13;

FIG. 13D is a sectional view taken along the line D—D of the positioner of FIG. 13;

FIG. 14A is a view of the proximal end of the positioner of FIG. 13; and

FIG. 14B is a sectional view of the distal tip of the positioner of FIG. 13.

Corresponding reference characters indicate corresponding components throughout the several views of the drawings.

DETAILED DESCRIPTION OF THE INVENTION

Figure 4A:
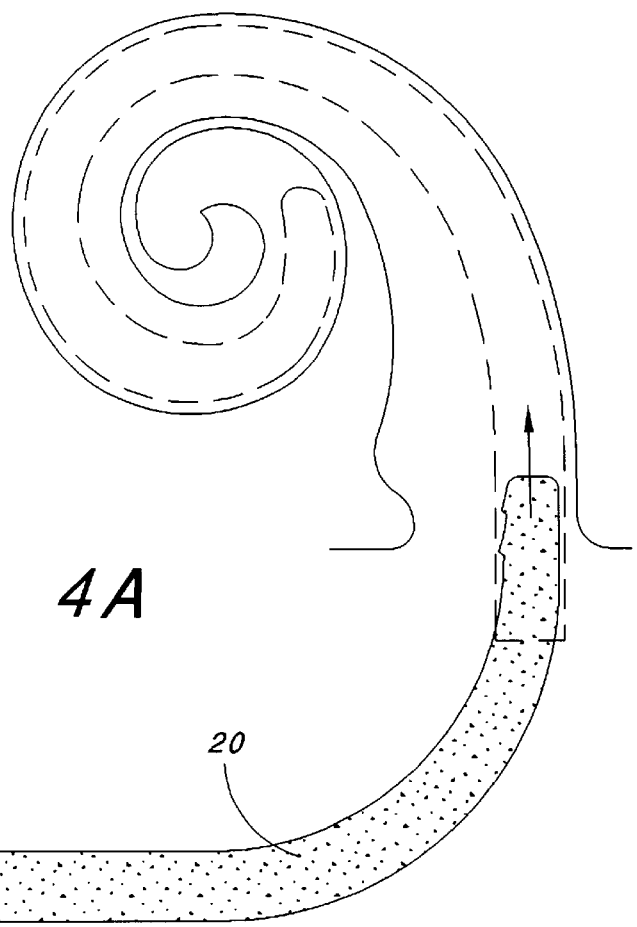
FIG. 4A illustrates insertion of the curved positioner into the scala tympani of the cochlea.

The following description is of the best mode presently contemplated for carrying out the invention. This description is not to be taken in a limiting sense, but is made merely for the purpose of describing the general principles of the invention. The scope of the invention should be determined with reference to the claims.

The invention described herein teaches one type of electrode system that may be used with a cochlear stimulation system. Other electrodes and electrode systems may also be used for this purpose as disclosed, e.g., in Applicant's previously-filed patent applications Ser. No. 60/056,055, filed Sep. 2, 1997, and Ser. No. 60/061,945, filed Oct. 14, 1997, incorporated herein by reference. The materials, dimensions, methods of manufacture, and the like, described in these prior-filed patent applications are also applicable to the present invention.

Turning to FIGS. 1A and 1B, there is shown a side and a cross-sectional view, respectively, of an electrode array 10 that forms part of an electrode system 12 made in accordance with the present invention. The cross-sectional view of FIG. 1B is taken along the line A—A of FIG. 1A. A distal end portion 11 of the array 10 is shown in FIG. 1C.

As seen in FIGS. 1A, 1B and 1C, the electrode array 10 includes a plurality of spaced-apart electrodes 200, formed within a flexible carrier 204. Each of the electrodes is connected to at least one wire 202 which is embedded within the carrier 204. A proximal end of the these wires 202 (not shown) allows selective electrical connection to be made with each electrode 200 through use of a tissue stimulator, e.g., a cochlear stimulator.

As an important feature of the invention, in some embodiments, the distal end portion 11 of the electrode array 10 includes a plurality of sloping barbs or teeth 13. These barbs 13, as explained below, help maintain the electrode array 10 in its desired position against the modiolus wall of the cochlea once it is inserted into the cochlea.

A second component of the electrode system of the present invention is a positioner 20, as illustrated in FIGS. 2A, 2B and 2C. FIG. 2A shows a side view of the curved positioner 20. FIG. 2B shows an enlarged view of a distal end portion 21 of the positioner 20, including a barb 23. Typically, the distal end of the positioner 20 will include a plurality of barbs 23 formed therein. FIG. 2C shows a cross-sectional view of the positioner 20 taken along the line B—B of FIG. 2A. As seen in FIG. 2C, the positioner 20 includes a shallow smooth groove or channel 25 located along one side thereof. This channel or groove 25, as seen by the dotted-line representation of the bottom of the channel in FIG. 2A, traverses the entire length of the positioner 20.

The flexible positioner 20 is preferably made from a silicone polymer, and may be molded to assume the curved shape shown in FIG. 2A, or it may be molded to assume a more straightened shape. If curved, the radius of curvature "R" is selected to be somewhat larger than the natural curvature of the cochlea. That is, when inserted into the cochlea, the positioner 20 will have to assume a tighter wind or coil than that afforded by its formed curved shape. This assures that when inserted into the cochlea, the positioner 20 is held away from the modiolus wall, leaving a cavity or channel against the modiolus wall wherein the electrode array may be inserted.

Figure 5:
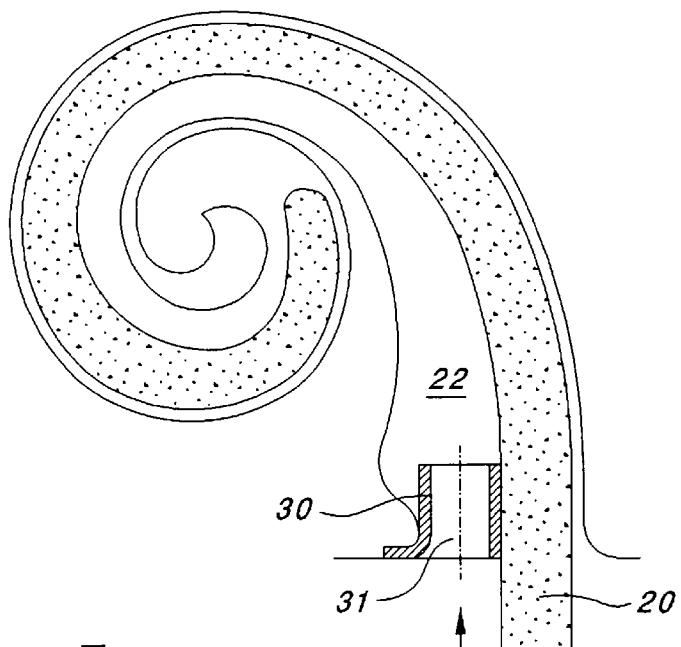
FIG. 5 shows a schematic representation of the spiraling scala tympani of the cochlea with the positioner inserted therein, and further illustrates the placement of the electrode-guiding insert into the front opening of the scala tympani.

A third component of the electrode system, in accordance with one embodiment thereof, is an electrode-guide 30 as shown in FIGS. 3A, 3B and 3C. The guide 30 is designed to be inserted into the proximal end of the cavity or channel formed between the modiolus wall and the grooved side of the positioner 20. The guide 30 includes a sleeve portion 32 and a flange portion 34. The sleeve portion 32 includes an opening or channel 31 therein having a size that allows the electrode array 10 (FIG. 1A, 1B) to readily slide therethrough. A portion of the flange 34, as seen best in FIG. 3B, is removed, thereby forming a straight edge 36 on one side of the flange. As will be evident from FIG. 5, below, this removed portion of the flange allows the insert 30 to fit snugly against the positioner 20 (i.e., the straight edge 36 fits up against the positioner 20) when the insert 30 is inserted into the cochlea.

The electrode-guiding insert 30 is made from a biocompatible material, such as platinum (Pt), titanium (Ti) or Teflon.

In some embodiments, as described more fully below, the electrode-guiding insert may be omitted.

Figure 4B:
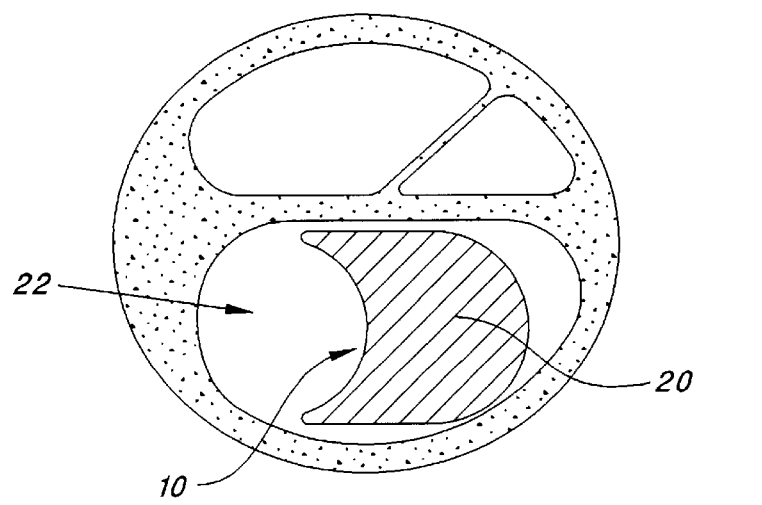
FIG. 4B shows a cross-sectional view of the cochlea with the positioner placed within the scala tympani.

Next, the method of using the electrode system of the present invention will be described in connection with FIGS. 4A through 6B. First, as shown in FIGS. 4A and 4B, the flexible positioner 20 is inserted into the scala tympani (one of the channels of the cochlea) to the desired depth. The desired depth typically involves a rotation of about 360 degrees and causes, as seen best in FIG. 4B, the positioner 20 to rest against the outer or lateral wall of the scala tympani. This position leaves a channel or opening 22, one side of which is defined by the groove 25, adjacent the inner wall (modiolus) of the scala tympani. The opening 22 is slightly larger than the cross-section of the electrode array 10.

Advantageously, the super-flexible nature of the positioner prevents it from causing damage to the cochlear structure. At the same time, once inserted, the positioner 20 provides a guide for the electrode array 10, and protects the cochlear walls from being damaged or touched directly by the stiffer electrode body 204.

Once the positioner has been inserted to the desired depth, the electrode-guiding insert 30 (if used) is pushed into the opening of the channel 22. When this insertion is performed, the flat or straight side 36 of the flange 30 is placed against the grooved side of the positioner 20.

Figure 6A:
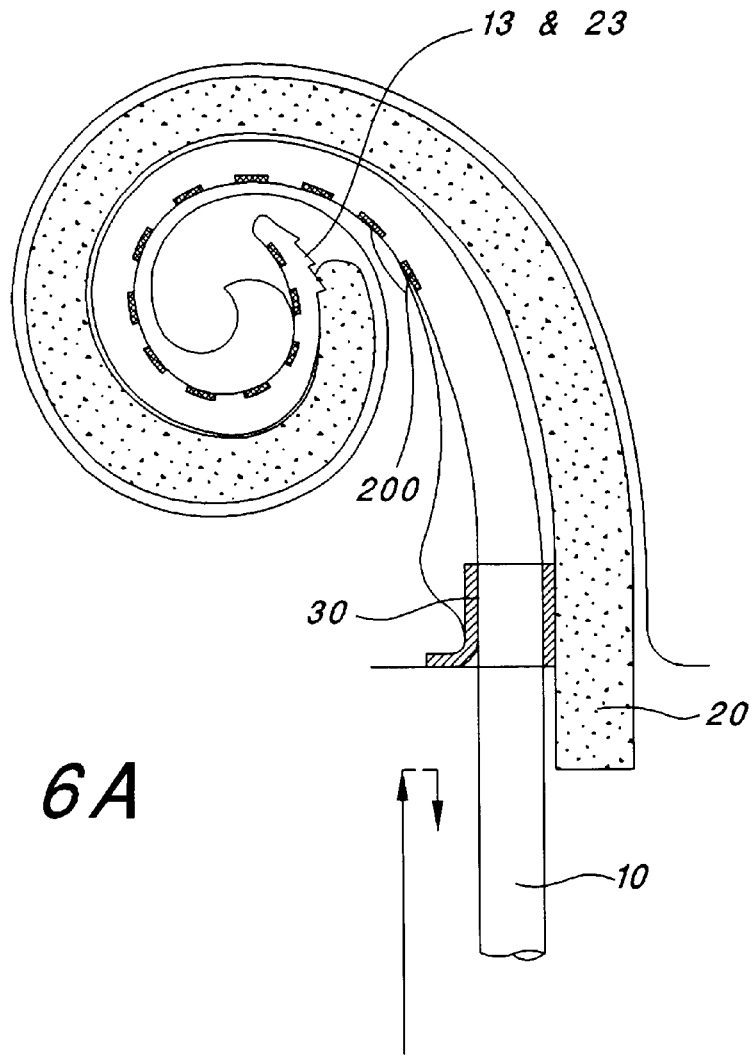
FIG. 6A is a schematic representation of the cochlea as in FIG. 5, but with the electrode array having been inserted into the scala tympani through the electrode-guiding insert.
Figure 6B:
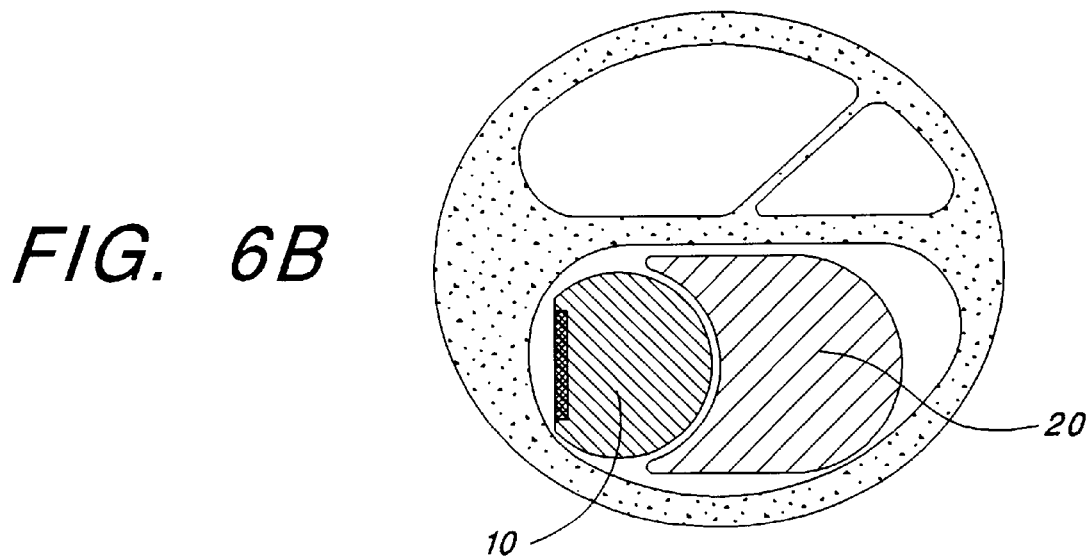
FIG. 6B is a cross-sectional view of the scala tympani of FIG. 6A, showing the manner in which the positioner forces the electrode array to hug the modiolus of the cochlea.

With the positioner 20 and electrode-guiding insert 30, in place, the electrode array 10 is next inserted through the opening 31 of the guiding insert 30 to the desired depth as shown in FIGS. 6A and 6B. Insertion is performed so that the electrodes 200 lie on the inside curve of the electrode array as it is inserted into the cochlea, thereby placing these electrodes 300 adjacent the modiolus wall.

The desired depth of insertion is preferably beyond the depth of the positioner 20. Advantageously, because the carrier body 204 of the electrode array 10 is tapered, it can be sized so that the diameter of the opening 31 within the guiding insert 30 effectively prevents further insertion once full insertion has occurred.

As explained above, the distal end portion 11 of the electrode array 10 includes engaging or locking teeth or barbs 13 that engage with corresponding teeth or barbs 23 located at the distal end of the positioner. Once the electrode array 10 has been inserted, the electrodes 200 are positioned very close to the modiolus of the cochlea, as desired. As a final optimization of the position of the electrode contacts 200 of the electrode array, the electrode array 10 may be pulled back slightly (about 2 mm). This backward motion assures that the distal end portions 11 and 21 of the electrode array and the positioner are engaged by the barbs 13 and 23 located thereon. Such engagement may further serve to force the electrode contacts 200 into direct contact with the modiolar wall.

Turning next to FIGS. 7A through 9, a preferred method of making the electrode array 10 will be described. It is to be emphasized that this method of making the electrode array is not the only way an electrode array suitable for use with the electrode system of the invention could be made. Rather, it merely represents an easy and inexpensive (and thus a preferred) way in which the electrode array may be fashioned.

Most designs of electrodes and connectors are based on the principle of molding a contact or array of contacts, usually made from biocompatible metal, into a polymer carrier like silicone or polyurethane rubber. The electrode contacts are usually required to be located in a controlled position in reference to the surface of the carrier, with specified surface areas to be fully exposed to the stimulated or interconnection area. Disadvantageously, making such electrodes or connectors becomes extremely difficult, especially when the contacts are very small and/or a large number of contacts are required, e.g., as is the case with a cochlea electrode. The main problem encountered in the fabrication of such electrodes or connectors is to find a reliable method of holding the system of contacts in the desired and stable position during the process of welding the connecting wires and molding the polymer carrier. A further problem relates to maintaining a controlled surface of the contacts that are to remain exposed, i.e., to ensure that the contacts are not covered by the polymer when the carrier is molded.

The preferred methods of making the electrode array described below in connection with FIG. 7A through FIG. 9B is based on the principle of attaching (by the process of resistance welding) electrode contacts made from precious, biocompatible material (such as platinum or its alloys) to a foil carrier made from a non-toxic but chemically-active metal like iron (Fe). Attached to the metal carrier, the electrode contacts remain in a desired and stable position allowing easy connecting of the wiring system and subsequent molding of the polymer carrier. After completion of the molding process, the metal foil carrier is etched away using a mixture of diluted acids, such as $HNO_3$ and HCl. The precious metal contacts and polymer are immune to the acid and remain in their intact, unaltered shape, and thereby provide the desired electrode array structure.

To illustrate this method, the method will be described relative to the fabrication of a multi-electrode electrode array suitable for insertion into the cochlea. As a first step, an array of contacts 200 are welded onto an iron carrier 100 so as to assume a desired spaced-apart relationship, as shown in FIG. 7A. Each contact 200 consists of two pieces of platinum foil 210 and 220, connected together and joined to the carrier 100 by a weld 230, as shown in FIG. 7B.

Figure 8A:
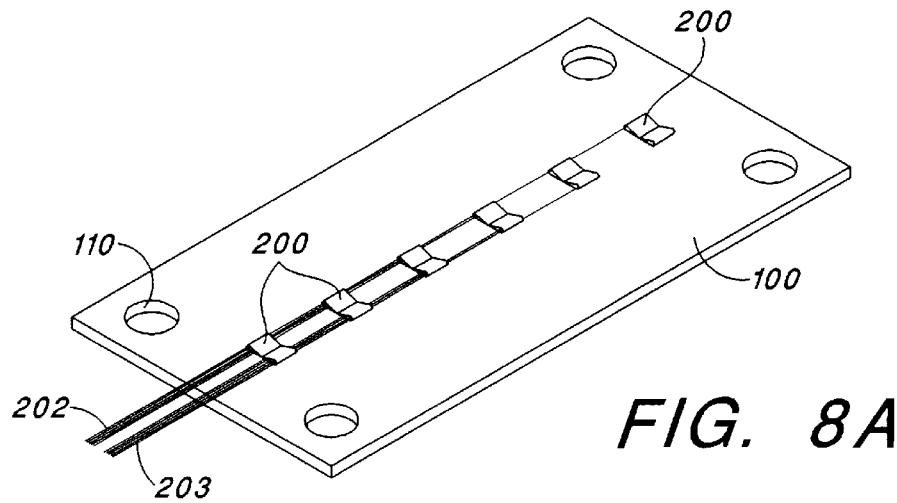
FIGS. 8A, 8B, 8C and 8D illustrate one manner in which wires may be bonded to each of the electrode contacts of FIG. 7B during manufacture of the electrode array.
Figure 8B:
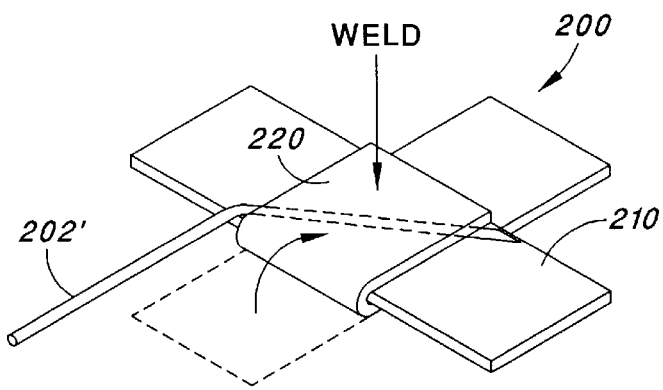
Figure 8C:
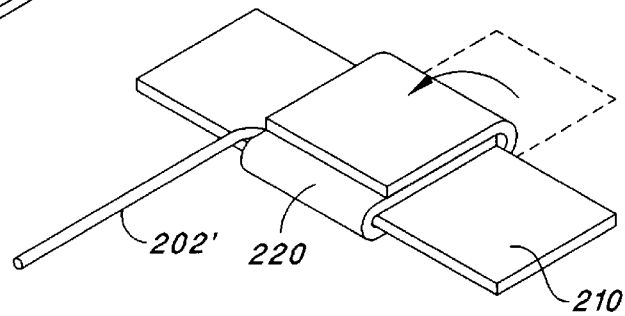
Figure 8D:
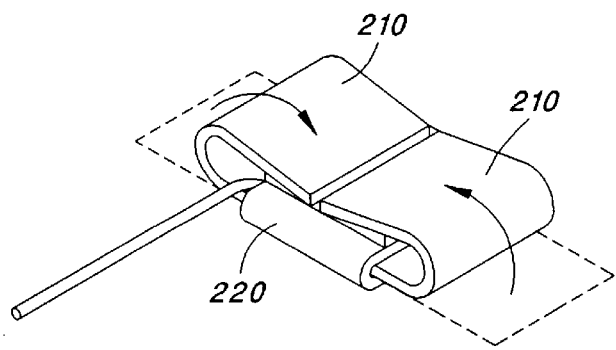

As a second step, a wiring system is connected to each of the electrode contacts 200. This is accomplished as shown in FIGS. 8A, 8B, 8C and 8D. As seen in FIG. 8B, for example, an insulated wire 202', having the insulation removed from its tip, is laid on top of the electrode foil pieces 210 and 220. One of the ends of the foil piece 220 is then folded over to hold the end of the wire while the wire is welded or crimped in position (FIG. 8B). Then, the other end of the foil 220 is folded over the first folded end (FIG. 8C). If other wires are present, e.g., going to electrode contacts further up the array, then such wires may pass over the foil piece 210, lying parallel to the wire 202' so as to form a bundle of wires 202. A similar bundle may be formed on the other side of the folded foil piece 220, thereby forming another wire bundle 203. The ends of the foil piece 210 may then be folded over the folded piece 220 (FIG. 8D) to complete the wire system connection process.

Once the wire bundles 202 and 203 have been connected to the electrodes 200, the foil carrier 100 is placed on a molding die 300 as shown in FIG. 9. The die 300 has alignment pegs 310 adapted to align with corresponding alignment holes 110 in the foil carrier 100. The die 300 further has a cavity or channel 320 formed therein into which the required amount of material to form the polymer carrier 204 (FIG. 1A) is injected. This cavity or channel 320 may be shaped or formed as desired, e.g., to include the teeth or barbs 23 described previously.

As an alternative to the flat-surface die 300 shown in FIG. 9, a curved die 301 may be used as shown in FIGS. 9A and 9B. Such die 301 includes a curved surface 303 on which the foil carrier 100 may be placed. The die 301 has alignment pegs 311 adapted to align with corresponding alignment holes 110 in the foil carrier 100. A channel or cavity 321 is formed in the curved surface 303 into which the required amount of material to form the polymer carrier is injected. By placing the foil carrier assembly 100 in the curved die of FIGS. 9A and 9B (note that FIG. 9A comprises a perspective view of the die 301, and FIG. 9B comprises a side or profile view of the die 301), the array can be molded or formed to assume a lightly curved shape. Such slightly curved shape is preferred to achieve directional stability of the array during insertion.

Thus, it is seen that through proper use of the suitable die 300 or 301, or other dies, the electrode array may be made to assume a natural curved shape, a slightly curved shape, or to be straight.

After the material cures, the foil carrier with the electrode array assembly (which is now molded inside of the polymer) is removed from the die 300 or 301 and placed in a mixture of diluted acids. The mixture of diluted acids dissolves the foil carrier 100, thereby exposing a clean surface of the electrode contacts 200. After washing to remove any residue of acids and Fe salts, the main electrode array structure is completed.

Alternative Embodiments

Other embodiments of the invention may also be used. For example, the positioner 20, shown in a somewhat straightened position in FIG. 10, may be used with any type of electrode system or electrode array in order to help position the electrode contacts of the array in a desired position within the cochlea. When so used, the positioner may be inserted into the cochlea first (i.e., before insertion of the electrode array), as described above in connection with FIGS. 4A and 4B, or second (i.e., after insertion of the electrode array), as described more fully below.

Typically, as indicated above, the positioner 20 is curved as illustrated in FIGS. 2A, 2B and 2C, although the degree and amount of curvature is not critical given the flexible nature of the positioner. The distal end of the positioner 20 may include a plurality of barbs or bumps 23 formed therein. Moreover, the positioner 20 includes a smooth groove or channel 25 located along one side thereof to facilitate holding the electrode array 10 on that side of the positioner facing the modiolar wall. This channel or groove 25 traverses the entire length of the positioner 20, or at least the length of the positioner up to the distal tip where the barbs or bumps 23 may be located.

As described above, the flexible positioner 20 is preferably made from a silicone polymer, and is molded to assume a generally curved shape, with a width or cross-sectional area that is tapered, as required, to match the cross-sectional area or width of the cochlea. The radius of curvature "R" is selected to be somewhat larger than the natural curvature of the cochlea. That is, when inserted into the cochlea, the positioner 20 will have to assume a tighter wind or coil than that afforded by its formed curved shape. This assures that when inserted into the cochlea, the positioner 20 is held away from the modiolus wall, leaving a cavity or channel against the modiolus wall wherein the electrode array may be inserted. Further, this preferred shape and positioning of the positioner within the cochlea improve the directional stability of the electrode array during insertion, i.e., help prevent rotation of the electrode array, thereby assuring that the electrode contacts remain positioned adjacent the modiolus wall.

Figure 11:
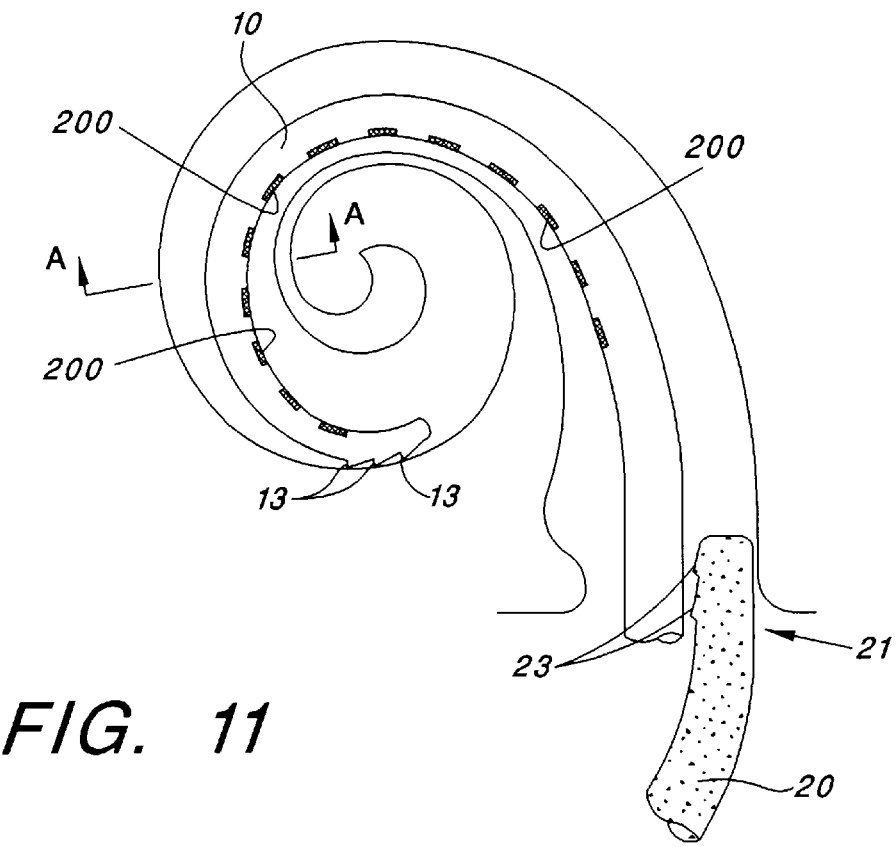
FIG. 11 is a schematic representation of the cochlea showing an alternate technique for insertion of the electrode array, and in particular showing the electrode array first inserted into the cochlea and showing the positioner inserted second into the cochlea.

One technique for inserting an electrode array 10 into the cochlea without having to use a guiding insert 30 is to first insert the electrode array 10 into the cochlea using any desired technique, as shown in the FIG. 11. Typically, during such insertion, the electrode contacts 200 of the electrode array 10 will be oriented to face the desired wall within the cochlea, e.g., the modiolar wall.

Figure 11A:
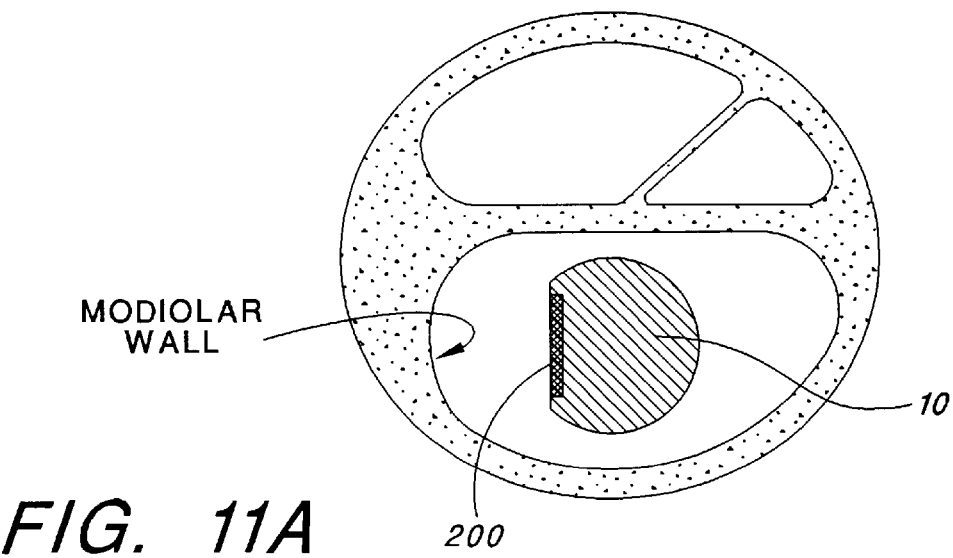
FIG. 11A is a sectional view taken along the line A—A of FIG. 11.

As evident from the schematic representation of FIG. 11, as well as the sectional view of FIG. 11A, the electrode contacts 200 of the electrode array 10, when the electrode array 10 is first inserted into the cochlea are not firmly held in position against the inner wall (modiolus) of the cochlea. In order to force or hold the electrode contacts up against the modiolus, the positioner 20 is also inserted into the cochlea, behind the electrode array 10, i.e., on the side of the electrode array 10 farthest from the modiolus, as seen in FIG. 11 (which shows the distal tip 21 of the positioner 20 just as it is first inserted behind the electrode array 10 within the cochlea).

Figure 12:
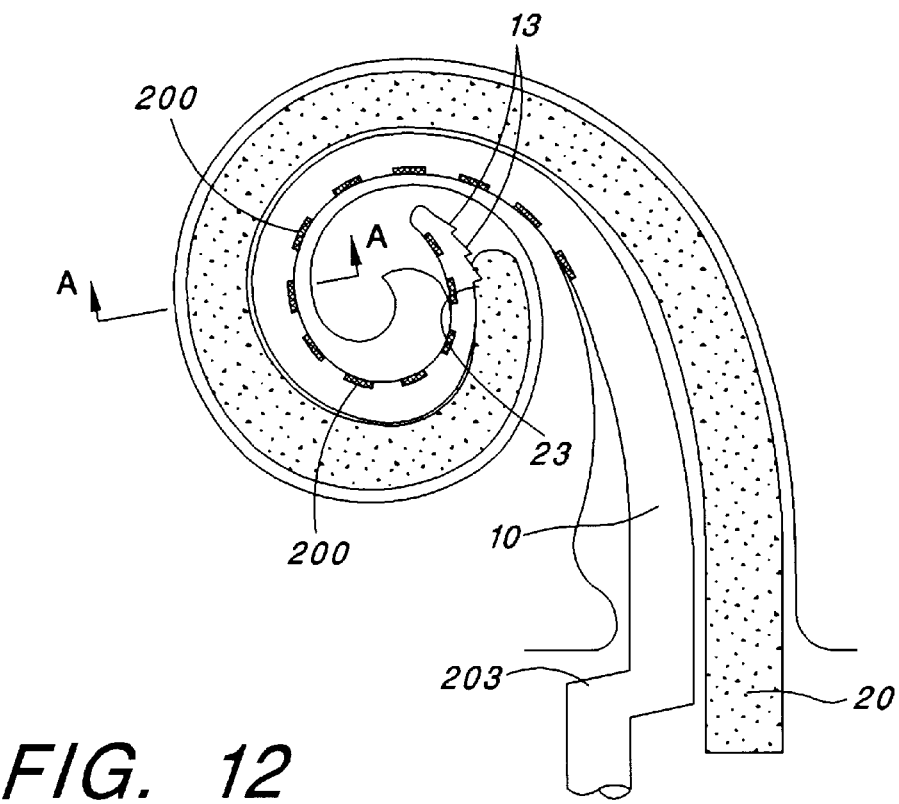
FIG. 12 is a schematic representation of the cochlea as in FIG. 11, but showing the positioner fully inserted into the cochlea.
Figure 12A:
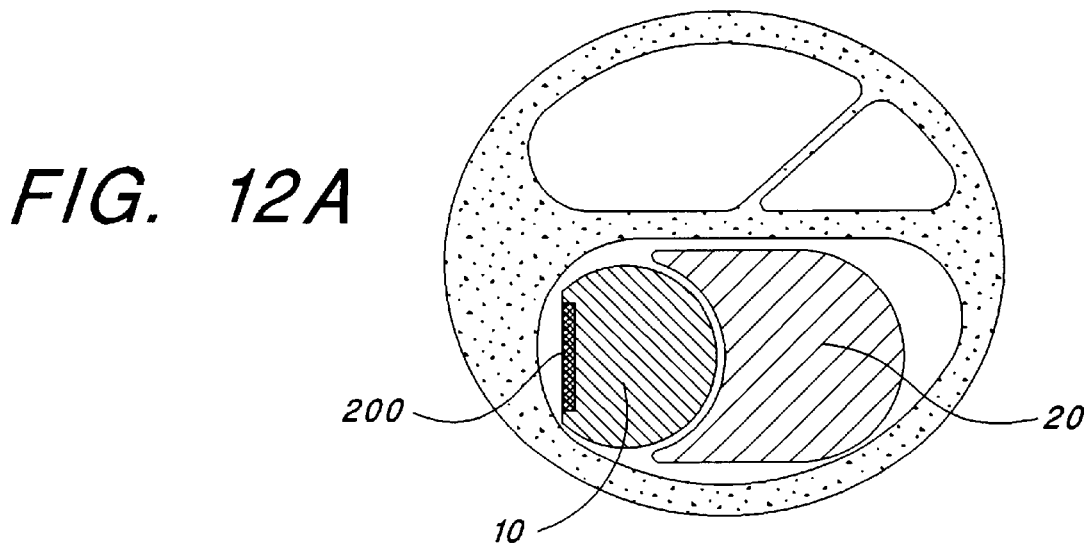
FIG. 12A is a sectional view of the cochlea taken along the line A—A of FIG. 12.

As the positioner is pushed deeper into the cochlea, it forces the electrode array 10 up against the modiolar wall, which action causes most, if not all, of the electrode contacts 200 to be in direct contact (touching) the modiolar wall. Moreover, as the positioner 20 is pushed still deeper into the cochlea, it eventually grabs (either through a friction fit, and/or with the assistance of the barbs or bumps 23) the electrode array 10 and carries the electrode array 10 with it deeper into the cochlea, causing the electrode array 10 to be inserted, e.g., an additional ½ turn deeper into the cochlea than when initially inserted. Advantageously, once in such fully inserted position, as shown in FIGS. 12 and 12A, the barbs or bumps 23 on the positioner, in combination with the barbs or teeth 13 on the electrode array, prevent the electrode array 10 from sliding backwards out of the cochlea.

Note, typically the electrode array 10, as seen best in FIG. 1A, has an offset 203. Such offset 203 functions as a stop to prevent the electrode array from being inserted too deep into the cochlea. Even when such offset cannot effectively function as a stop, it can always function as a mark, to aid the physician to know when the desired insertion depth has been achieved.

An alternative and preferred embodiment of a positioner 20' is illustrated in FIGS. 13, 13A, 13B, 13C, 14A and 14B. As seen best in FIG. 13, the positioner 20' assumes a general shallow hook shape. (Note, "shallow", in this context, refers to the fact that a distal tip or end portion 21' of the positioner bends only slightly more than 90 degrees from the longitudinal axis or center line of the positioner at the proximal end.) The distal end portion 21' is detailed in the sectional view of FIG. 14B.

The positioner 20' includes a channel or hole 27 for receiving a guiding wire stylet, as explained below, that passes longitudinally through the entire length of the body of the positioner. At the distal tip 21' as seen best in FIG. 14B, a tracing marker 29 is embedded within the channel 27. Such marker 29 is preferably made from platinum or other suitable material that can be easily seen in X-ray or other images. A plug 27' is placed on the proximal side of the marker 29, and a smooth rounded distal tip 21" is formed on the distal side of the marker 29. The marker 29 advantageously facilitates viewing of the location of the positioner using X-rays or other imaging equipment.

Figure 10:
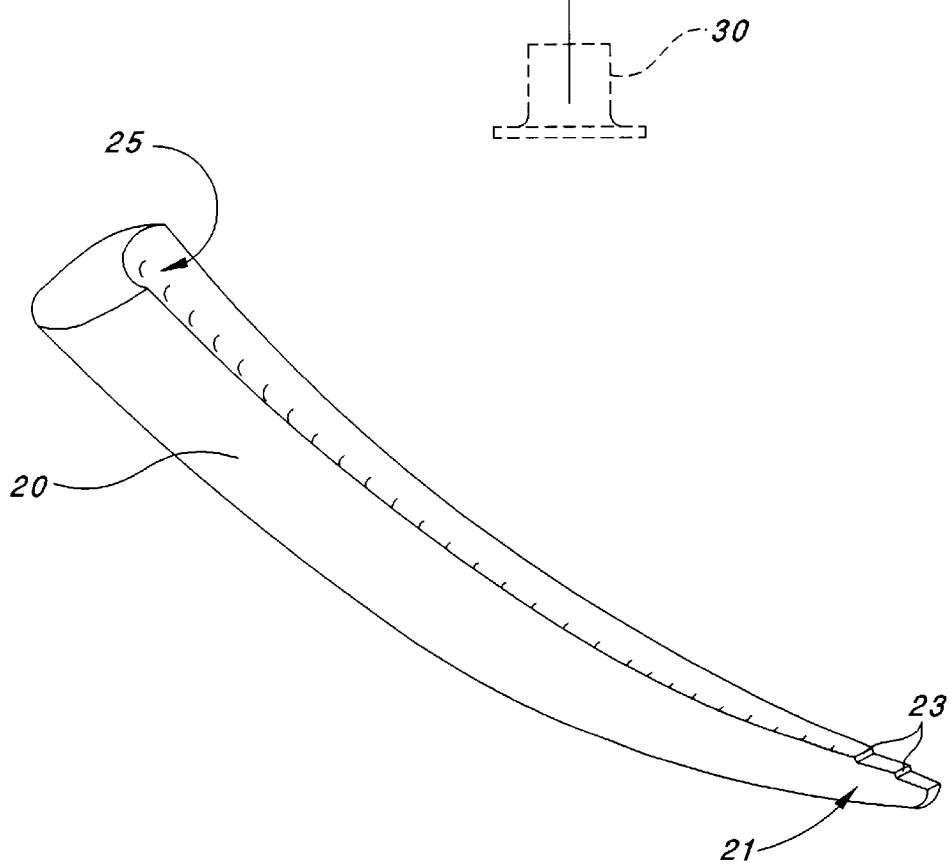
FIG. 10 is a perspective view of a positioner made in accordance with the present invention lying in a somewhat straightened position.

A side channel 25 is formed along one side of the positioner body along its entire length, as previously described in connection with the positioner shown in FIG. 10. The positioner 20' is preferably tapered, as illustrated generally in the sectional views of FIGS. 13A, 13B, 13C, and 13D taken respectively at the lines A—A, B—B, C—C and D—D of FIG. 13.

Typical dimensions of a cochlear positioner made in accordance with this preferred embodiment of the invention are shown in FIGS. 13, 13A, 13B, 13C, 14A and 14B, expressed in millimeters (mm). As seen in these figures, the channel 25 maintains the same approximate width of 1.00 mm along the entire length of the positioner, even though the overall width of the positioner tapers from about 1.50 mm by 1.30 mm at the proximal end, to about 1.00 mm by 0.93 mm at the distal tip 21'. The stylet channel 27 has a diameter of approximately 0.3 mm.

The positioner 20' is made using a suitable mold, similar to that used in making the electrode shown in FIG. 9A, on which a silastic tube, having an inner diameter of 0.3 mm and an outer diameter of about 0.64 mm, is placed. The body of the positioner 20' is then formed around the tube using silicone or other suitable silastic material using molding techniques known in the art. The tube passes through the entire length of the positioner 20'. If necessary, the molding process may be carried out in two steps, forming one half of the positioner body on one side of the tube during a first step, and forming the other half of the positioner body on the other side of the tube during a second step. The side channel 25 is formed along one side of the positioner during the molding process.

After the positioner has been formed as described above, a drop of silastic, or other suitable material, is placed in the distal end of the tube, followed by insertion of the tracking marker 29. The drop of silastic forms the plug 27'. The tracking marker 29 is inserted into the distal end of the tube sufficiently far so that additional silastic material may be inserted into the tube and attach to the walls of the positioner body at the distal end 21' so as to form a smooth rounded distal tip 21" of the positioner.

A handle 24 is formed at the proximal end of the positioner, as seen in FIGS. 13 and 14A. This handle 24 not only provides a suitable finger-hold for grabbing hold of the positioner during the insertion process, but also provides a visual indication of the orientation of the positioner because the handle 24 points in the same direction as the curved distal tip 21'.

The embodiment of the positioner 20' shown in FIG. 13 advantageously facilitates insertion of the positioner into the scala tympani duct of the cochlea. As needed, an insertion tool, such as that described in U.S. patent application Ser. No. 60/087,655, filed Jun. 2, 1998, may be used to aid in the insertion process. If so, the handle 24 facilitates loading of the positioner within the insertion tool, and further assures that the positioner does not twist as it is inserted. The referenced patent application, Ser. No. 60/087,655, is incorporated herein by reference.

During the insertion process, a wire stylet may be inserted into and through the channel 27 until the distal tip of the stylet engages the plug 27'. Such insertion of the stylet will cause the distal portion of the positioner to straighten, which in turn facilitates beginning or starting the insertion process of the positioner into the open end of the scala tympani duct of the cochlea. As the distal end portion 21' of the positioner is inserted deeper into the scala tympani duct, the stylet may be retracted, as needed. Further, as the insertion occurs, the position or location of the distal tip of the positioner may be monitored on an X-ray or other suitable imaging device by monitoring the location of the tracing marker 29 as such marker readily shows up on the image displayed by the X-ray or other imaging device.

As described above, it is thus seen that an electrode system is provided wherein engagement of the tips of the electrode array 10 and positioner 20 or 20' by the internal friction of both components against the cochlear walls, stabilizes the electrode contacts in the desired and optimal position in direct contact with the modiolar wall. In some embodiments, such positioning may be aided by the barbs 13 and 23 of the array and positioner, respectively. In other embodiments, such barbs are not needed. In a preferred embodiment, the positioner includes a channel 27 into which a stylet may be removably inserted, and the location of the positioner within the cochlear may be readily tracked by inclusion of a tracking marker 29, made from, e.g., platinum, which is embedded within the distal tip 21' of the positioner.

While the invention herein disclosed has been described by means of specific embodiments and applications thereof, numerous modifications and variations could be made thereto by those skilled in the art without departing from the scope of the invention set forth in the claims.

What is claimed is:

1. An electrode system adapted for use with a tissue stimulation device comprising:
    a flexible electrode array having a multiplicity of electrode contacts along one surface thereof;
    a flexible positioner adapted for insertion into a body cavity, said flexible positioner having front and rear sides, said body cavity having front and back walls, said flexible positioner being adapted for insertion into the body cavity so that the positioner assumes a position within the body cavity having its rear side lie against the back wall of the cavity, and leaving an open channel between the front side of the positioner and the front wall of the body cavity; and
    an electrode-guiding insert adapted for insertion into the open channel created between the front side of the positioner and the front wall of the body cavity;
    wherein the flexible electrode array is insertable through the electrode-guiding insert into the open channel so that the electrode contacts are positioned adjacent the front wall of the body cavity.

2. The electrode system as set forth in claim 1 wherein the flexible positioner is adapted for insertion within a human cochlea and comprises a curved flexible positioner having a groove or channel running longitudinally along its front side.

3. The electrode system as set forth in claim 1 wherein a distal portion of the electrode array and a distal portion of the positioner each contain engaging barbs adapted to interface with each other and secure the electrode array in a desired position wherein the electrode contacts are held against the front wall of the body cavity.

4. A flexible positioner for insertion into a body cavity, said flexible positioner having front and rear sides, said body cavity having front and back walls, said flexible positioner being adapted for insertion into the body cavity so that the positioner assumes a position within the body cavity having its rear side lie against the back wall of the cavity, and leaving an open channel between the front side of the positioner and the front wall of the body cavity, and wherein a tracing marker, having properties that facilitate seeing the tracing marker on an imaging system, is embedded in a distal end of the positioner.

5. The flexible positioner as set forth in claim 4 wherein the flexible positioner comprises a curved flexible positioner having a side groove or channel running longitudinally along its front side.

6. The flexible positioner as set forth in claim 5 wherein the positioner is adapted to fill space within the body cavity along with an electrode array, and wherein the positioner has a cross-sectional area sized such that insertion of the positioner within the body cavity into which the electrode array has already been at least partially inserted causes the electrode array to be carried deeper into the body cavity by friction created between engaging walls of the electrode array and positioner.

7. The flexible positioner as set forth in claim 4 wherein a distal portion of the positioner has engaging barbs adapted to interface with other engaging barbs of an electrode array positioned to reside within the side groove of the positioner inside the body cavity.

8. The flexible positioner as set forth in claim 4 further including a channel passing longitudinally through the positioner for removably receiving a guiding stylet.

9. The flexible positioner as set forth in claim 8 wherein the channel is sealed at its distal end.

10. An electrode system adapted for insertion into the scala tympani of a human cochlea as part of a cochlear stimulation system, the electrode system comprising:

a flexible electrode array having a multiplicity of electrode contacts, and a flexible positioner adapted for use with the flexible electrode array, said flexible positioner comprising an elongate, flexible body having dimensions that facilitate its insertion fully into the scala tympani, the scala tympani having front and back walls;

wherein the elongate flexible body of the positioner is made from a silicone polymer formed in a generally curved shape, and the elongate flexible body is separate and detached from the electrode array;

wherein the elongate flexible body of the positioner has a proximal end and a distal end, and wherein the elongate flexible body is tapered, having a larger cross sectional area at the proximal end than at the distal end, and wherein, when inserted into the scala tympani, the flexible positioner is adapted to assume a position within the scala tympani against the back wall of the scala tympani; and wherein the flexible electrode array is adapted to be inserted into the scala tympani and positioned therein so that the flexible electrode array lies between the positioner and the front wall of the scala tympani.

11. The electrode system of claim 10 wherein the elongate flexible body of the positioner naturally assumes a shallow hook shape, wherein the distal end of the positioner bends more than 90 degrees from a longitudinal axis of the positioner at the proximal end.

12. The electrode system of claim 10 further including a hole passing longitudinally through the elongate flexible body of the positioner from its proximal end to its distal end.

13. The electrode system of claim 12 further including a smooth rounded distal tip formed at the distal end of the positioner, wherein the smooth rounded distal tip plugs the hole at the distal end of the positioner.

14. The electrode system of claim 12 further including a tracing marker placed in the hole at the distal end of the positioner, and the smooth rounded tip being formed on the distal side of the tracing marker, wherein the smooth rounded tip plugs the hole at the distal end of the positioner.

15. The electrode system of claim 10 further including a side channel formed along a front side of the positioner from the proximal end to the distal end.

16. The electrode system of claim 10 further including a handle formed at the proximal end of the positioner, the handle pointing in the same direction as the curve formed in the positioner.

17. The electrode system of claim 10 wherein each of the multiplicity of spaced-apart electrode contacts of the flexible electrode array lie along a front surface of the electrode array, the front surface of the electrode array comprising that surface nearest the front wall of the scala tympani when the positioner and electrode array are inserted into the scala tympani.

18. The electrode system of claim 17 wherein a distal portion of the positioner has engaging barbs thereon, and a distal portion of the electrode array also has engaging barbs thereon, the engaging barbs of the positioner being adapted to detachably interface with the engaging barbs of the electrode array when the positioner and electrode array combine to form the electrode system.

* * * * *